United States Patent [19]

Lazer

[11] Patent Number: 4,812,460
[45] Date of Patent: Mar. 14, 1989

[54] 3-[2-(3′,5′-DI-T-BUTYL-4′-HYDROXY-PHENYL)ETHENYL]PYRIDINE

[75] Inventor: Edward S. Lazer, Trumbull, Conn.

[73] Assignee: Boehringer Ingelheim Pharmaceutical, Inc., Ridgefield, Conn.

[21] Appl. No.: 135,886

[22] Filed: Dec. 21, 1987

Related U.S. Application Data

[62] Division of Ser. No. 843,898, Mar. 25, 1986, Pat. No. 4,743,606.

[51] Int. Cl.$^4$ .................... C07D 211/70; A61K 31/44
[52] U.S. Cl. ..................................... 514/277; 546/344
[58] Field of Search ........................ 546/344; 514/277

[56] References Cited

PUBLICATIONS

Bogdanov, et al., Donetsk Branch, Inst. Chem. Phys., Academy of Sciences of USSR, No. 12, pp. 1660–1664 (Dec. 1971).

Primary Examiner—Mary C. Lee
Assistant Examiner—Robert C. Whittenbaugh
Attorney, Agent, or Firm—David E. Frankhouser; Alan R. Stempel; Mary-Ellen M. Timbers

[57] ABSTRACT

The present invention discloses 3-[2-(3′,5′-di-tert-butyl-4′-hydroxyphenyl)ethenyl]pyridine and its use in treating inflammation, particularly chronic inflammatory diseases such as arthritis, and allergic disorders.

2 Claims, No Drawings

3-[2-(3',5'-DI-T-BUTYL-4'-HYDROXYPHENYL)ETHENYL]PYRIDINE

This is a division of application Ser. No. 843,898, filed Mar. 25, 1986 now U.S. Pat. No. 4,743,606.

BACKGROUND OF THE INVENTION

1. Field of the Invention

This invention relates to compounds, compositions and methods useful in treating symptoms of immunological and non-immunological disorders such as allergy, inflammation, shock or other disorders wherein arachidonate metabolites are implicated.

2. Brief Description of the Prior Art

G. N. Bogdonov, A. N. Rozenberg and A. K. Sheinkman, Khimiya Geterotsiklicheskikh Soedinenii, 12, 1660–1644 (1971) discloses 2-[2-(3',5'-di-t-butyl-4'-hydroxyphenyl)ethenyl]pyridine and 4-[2-(3',5'-di-t-butyl-4'-hydroxyphenyl)ethenyl]pyridine as potential anti-tumor compounds. No mention is made of anti-inflammatory activity.

Many other di-t-butylphenolic trans-stilbenes are disclosed in the literature as chemical intermediates [M. T. Cox, S. E. Jaggers and G. Jones, J. Med. Chem. 21, 182–188 (1978)], although no biological activity is described for them.

Disclosures exist for anti-inflammatory 4-substituted 2,6-di-t-butylphenol derivatives in which an aromatic or heteroaromatic ring is either directly connected to the phenolic ring, or separated by a carbonyl group. See, for example, Moore, U.S. Pat. No. 4,172,082 (1979); U.S. Pat. No. 4,124,725 (1978); and Y. Isomura, N. Ito, S. Sakamoto, H. Homma, T. Abe and K. Kubo, Chem. Pharm. Bull., 31, 3179–3185 (1983).

SUMMARY OF THE INVENTION

This invention relates to 3-[2-(3,5-di-t-butyl-4-hydroxyphenyl)ethenyl]-pyridine (I) also referred to as 2,6-di-tert-butyl-4-[2-(3-pyridinyl)ethenyl]phenol.

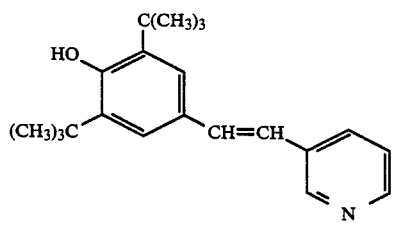

The compound of formula 1 preferably in the transform, is useful in treating inflammatory disorders, for example rheumatoid arthritis. This compound is active in both the developing and established adjuvant arthritis screens in the rat. It is also active in the carrageenan paw edema and reverse passive arthus screens. In addition to showing activity in these in vivo assays, compound 1 was found to inhibit both cyclooxygenase and 5-lipoxygenase, two enzymes known to produce pro-inflammatory substances from arachidonic acid. Compound 1 also inhibited the release of pro-inflammatory oxygen metabolites from stimulated neutrophils.

Compound 1 shows an $ED_{50}$ of 4 mg/kg in the rat established adjuvant arthritis model. A 50% ulcerogenic response in the animals tested ($UD_{50}$) at 200 mg/kg for 4 days is observable when the rats are examined 24 hours after the last dose. Thus, the $UD_{50}/ED_{50}=50$, a very wide safety margin.

DETAILED DESCRIPTION OF THE INVENTION

The compound of this invention is prepared by a procedure similar to the general method for di-t-butylphenolic trans-stilbenes described by M. T. Cox et al., supra. 3-Pyridylacetic acid as the hydrochloride salt or free base is heated with 3,5-di-t-butyl-4-hydroxybenzaldehyde in the presence of a basic catalyst, for example piperidine. A small amount of an inert solvent such as methylene chloride can be added at the beginning of the reaction to facilitate mixing, and boiled off as the reaction progresses.

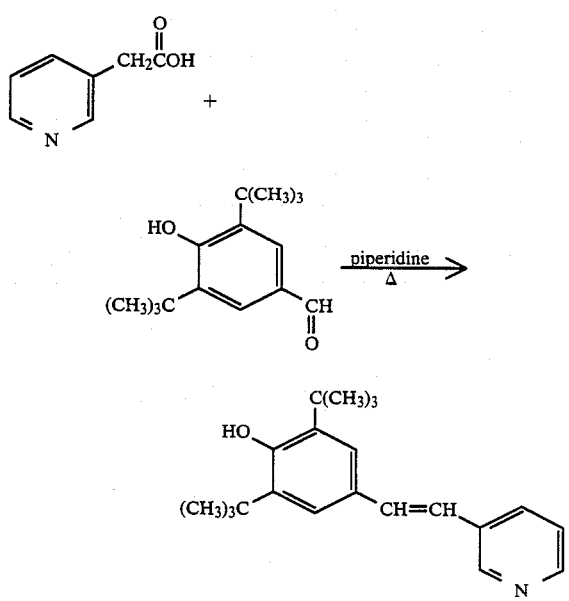

The compound of this invention can also be prepared by an alternate two step process, illustrated below. 3,5-Di-t-butyl-4-hydroxybenzaldehyde is condensed with the ethyl ester of 3-pyridylacetic acid in ethanol in the presence of a basic catalyst such as piperidine. The resulting ester 2 is hydrolyzed and decarboxylated giving 1.

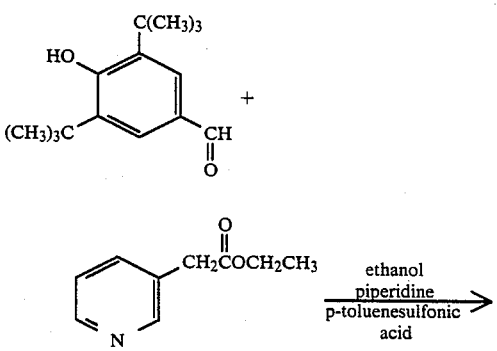

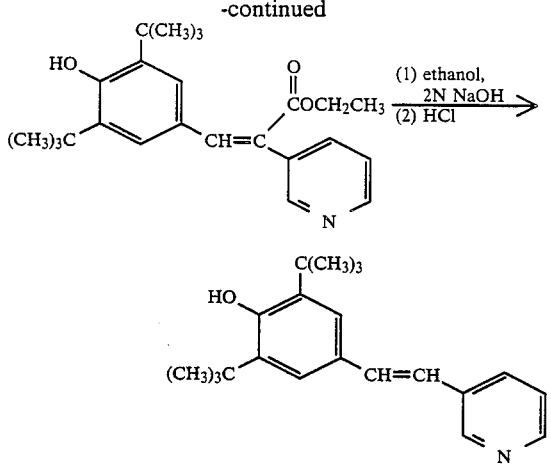

The antiinflammatory compound of the present invention can be administered to treat immunological disorders, chronic inflammation and inflammatory diseases including rheumatoid arthritis, allery and the like by any means or route of administration that produces contact of the compound with its site of action in the body of the individual human or animal under treatment. The compound can be administered by known conventional routes of administration such as by oral administration, or injection. The compound is usually administered in dosage forms which deliver it in a conventional pharmaceutical carrier or mixtures thereof which are selected on the basis of the particular route of administration and rate of delivery to the site of action which is desired.

Dosage forms (compositions) which are suitable for internal administration of the compounds include oral administration forms such as tablets, coated tablets, capsules, syrups, elixirs or suspensions. Suitable carriers for each applicable route of administration are described in Remington's Pharmaceutical Sciences.

The range of dosages in which the compound in accordance with the invention can be administered will vary depending upon the route of administration selected as well as the characteristics of the intended recipient, including age, body weight, general state of health and the like. Usually, the compound of the invention is administered in unit doses of from about 1 to about 100 mgs and from about 1 to about 4 times daily. Such unit doses can be combined in metered release dosage forms for sustained single dose release of the compound.

EXAMPLE 1

3-[2-(3′,5′-di-t-butyl-4′-hydroxyphenyl)ethenyl]pyridine

First, 3-pyridylacetic acid (7.0 g, 0.051 mol) and piperidine (5.22 g, 0.061 mol) are combined in methylene chloride (20 ml). Then, 3,5-di-t-butyl-4-hydroxybenzaldehyde (5 g, 0.026 mol) is added to the stirred mixture. The reaction mixture is heated and stirred on an oil bath, and the methylene chloride allowed to boil off. The oil bath temperature is permitted to rise over two hours to 145° C. and then is kept constant. The reaction mixture is removed from the oil bath after another 2¾ hours, dissolved in ethyl acetate (250 ml), and washed with water (2×200 ml), saturated sodium carbonate solution (1×100 ml) and saturated sodium chloride solution (1×100 ml). The organic solution is dried over anhydrous sodium sulfate and evaporated giving a brown oil (7 g). The product is crystallized twice from petroleum ether (1.3 g, 0.004 mol). M.p. 103°–104° C.

Elemental Analysis: Calculated: C, 81.49; H, 8.81; N, 4.53. Found: C, 81.55; H, 8.74; N, 4.28.

EXAMPLE 2

3-[2-(3′,5′-di-t-butyl-4′-hydroxyphenyl)ethenyl]pyridine

Ethyl 3-(3,5-di-t-butyl-4-hydroxyphenyl)-2-(3-pyridyl)-propenoate

Here, 3,5-di-t-butyl-4-hydroxybenzaldehyde (223 g, 0.952 mol), Ethyl 3-pyridylacetate (157.2 g, 0.952 mol), piperidine (81 g, 0.952 mol) and p-tolunesulfonic acid (0.5 g) are combined in ethanol (2,400 ml) and heated at reflux for 48 hours. The reaction mixture is allowed to cool to room temperature and then stirred on an ice bath, whereupon the product begins to crystallize. The mixture is stored in the freezer overnight, filtered and rinsed with cold ethanol-water (1:1). The product is dried, giving ethyl 3-(3,5-di-t-butyl-4-hydroxyphenyl)-2-(3-pyridyl)propenoate (169.1 g) Mp 119.5°–120.5° C.

Elemental Analysis: Calculated: C, 75.55; H, 8.21; N, 3.67. Found: C, 75.41; H, 8.52; N, 3.58.

3-[2-(3′,5′-di-t-butyl-4′-hydroxyphenyl)ethenyl]pyridine

Ethyl 3-(3,5-di-t-butyl-4-hydroxyphenyl)-2-(3-pyridyl)propenoate (168.6 g, 0.442 mol) is combined with ethanol (850 ml) and sodium hydroxide (850 ml) and heated to reflux for 4 hours. The volume of the reaction mixture is then reduced (to 1100 ml) on a rotary evaporator. The resulting mixture is stirred on an ice bath while 2N HCl (850 ml) is added slowly. The resulting solid is filtered, rinsed with water and dried. The crude product is crystallized twice (resulting in 69 g, 0.223 mol) from 2-propanol. By concentrating the mother liquors and further recrystallization additional product (12.7 g) is obtained (total of 81.7 g, 0.264 mol). M.p. 104°–105° C.

Elemental Analysis: Calculated: C, 81.49; H, 8.81; N, 4.53. Found: C, 81.50; H, 9.10; N, 4.41.

EXAMPLE 3

Developing Adjuvant-Induced Polyarthritis in Rats

This test is used to determine the ability of compounds to affect the immunological processes involved in the induction and development of arthritis.

Polyarthritis is induced in male CD rats (150–170 g) by injection of heat-killed *Mycobacterium butyricum*. Each animal is given 0.1 ml of a 0.5% (5 mg/ml) adjuvant suspension in light mineral oil injected subcutaneously into the plantar surface of the right hind foot. At least 6 rats are used in each test group. Animals are dosed orally with test compound immediately after adjuvant injection, and once daily for a total of 14 days. Foot volumes are measured 24 hours after the final dose by mercury displacement to the lateral malleolus. Mean displacement volumes and their standard errors are calculated for the non-injected hind paws. Untreated normal and arthritic control groups are used as comparison for test compound effect. Results are expressed as percent of control effect.

| Dose of Compound 1 | % Inhibition |
| --- | --- |
| 5 mg/kg | 56 |

| Dose of Compound 1 | % Inhibition |
|---|---|
| 50 mg/kg | 82 |

EXAMPLE 4

Developing Adjuvant-Induced Polyarthritis in Rats

The experiments reported here are performed using the same procedures as described in Example 3, except that 4-[2-(3',5'-di-t-butyl-4'-hydroxyphenol)ethenyl]-pyridine (prior art) is under assay rather than the compound of the invention.

| Dose | % Inhibition |
|---|---|
| 50 mg/kg | 0 |

EXAMPLE 5

Established Adjuvant-Induced Polyarthritis in Rats

This assay is used to determine the ability of compounds to affect an established chronic inflammatory condition.

Polyarthritis is induced as described in Example 3. Rats in which polyarthritis has become established are selected 14 days after receiving the adjuvant suspension. They are treated daily with oral doses of test compound for 14 days (days 14–27). Foot volumes of the non-injected paws are measured (as in Example 3). 24 hours after the final dose. Untreated arthritic control groups are used as comparison for test compound effect as described in Example 3.

| Dose of Compound 1 (mg/kg) | % Inhibition |
|---|---|
| 2.5 | 28 |
| 5.0 | 60 |
| 10.0 | 74 |
| 20.0 | 79 |
| 40.0 | 82 |

$ED_{50} = 4$ mg/kg

EXAMPLE 6

Carrageenan Induced Paw Edema in Rats

This test is used to determine the ability of a compound to affect non-immune acute inflammation. Edema is produced in the right hind paw of male CD rats (150±10 g) by the subplantar injection of carrageenan (0.1 ml of a 1 percent suspension in saline). Ten rats are used in each test group. Test compound or its vehicle is administered orally 1 hour prior to carrageenan injection. Paw volume is determined by calculating the amount of mercury displaced after immersing the paw to the level of the lateral malleolus. Foot volumes are measured just prior to test compound administration and again 3 hours after carrageenan injection and the difference designated as edema volume.

| Dose of Compound 1 | % Inhibition |
|---|---|
| 100 mg/kg | 56 |

EXAMPLE 7

Cyclooxygenase Inhibition Assay

Human platelets ($1 \times 10^7$ platelets/0.5 ml) in $Ca^{+2}$ free buffer (pH 7) are incubated with test compound for 15 minutes at 37° C. with shaking. $^{14}C$ Arachidonic acid (0.25 μCi, 0.155 μg/ml) is added and the mixture incubated for another 30 minutes. The reaction is terminated by addition of 0.8N HCl (0.025 ml). The mixture is then extracted with ethyl acetate:methylene chloride (2:3) supplemented with cold arachidonic acid (30 μg/ml) to reduce degradation of the metabolites. The organic phase is concentrated. The number of μl containing $1 \times 10^5$ cpm is determined and that volume is applied to a silica gel plate. The plate is developed in methylene chloride:methanol:acetic acid:water (90:8:1:0.8). The plate is air-dried and counted on a Berthold Linear TLC Analyzer. The integrated areas of the prostaglandin/thromboxane envelope are determined and compared with controls (no drug).

| Concentration of Compound | % Inhibition of Cyclooxygenase |
|---|---|
| $5 \times 10^{-8}$ M | 7 |
| $10^{-7}$ M | 11 |
| $3.3 \times 10^{-7}$ M | 25 |
| $6.6 \times 10^{-7}$ M | 50 |
| $10^{-6}$ M | 53 |
| $10^{-5}$ M | 59 |

$IC_{50} = 9 \times 10^{-7}$ M

EXAMPLE 8

Hydroxyacid Profile Assay of 5-Lipoxygenase Derived Arachidonic Acid Metabolites The hydroxyacid profile assay (HPA) is used in these experiments to determine whether, and to what extent, the compound of the invention inhibits the amount of 5-HETE biosynthesized by glycogen-stimulated polymorphonuclear leucocytes (PMNs). 5-HETE biosynthesis serves as a marker for arachidonic acid metabolism via the 5-lipoxygenase pathway which produces, among other things, a highly active chemotactic agent for neutrophils, $LTB_4$.

Buffer A (8.70 g NaCl; 0.27 g KCl; 0.42 g $Na_2HPO_4$; 0.76 g $KH_2PO_4$; and 1.00 g dextrose per liter $H_2O$; pH 7.0) (0.325 ml) is introduced into each of a battery of screwtop culture tubes. Then, a compound (0.100 ml) to be assayed is dispensed into individual tubes. Dose-response curves are determined by triplicate measurements at each concentration. Control tubes receive Buffer A (0.100 ml) in lieu of compound. Next, glycogen elicited rabbit PMNs ($2 \times 10^7$ cells/tube; $4 \times 10^7$ cells/ml (0.500 ml) are added to each tube. The tubes are vortexed and preincubated in a shaking 37° C. water bath for 15 minutes.

Thereafter, the tubes are removed from the water bath and Calcium Ionophore Solution (400 μg/ml A-23187; Sigma Chemical Co., St. Louis, MO) (0.025 ml), $^{14}C$-arachidonic acid (0.25 μCi in 0.025 ethanol; New England Nuclear Products, Boston, MA) (0.025 ml) and $Ca^{+2}$ solution ($CaCl_2.2H_2O$); 105.8 mg/10 ml $H_2O$) (0.025 ml) are added in that order. The tubes are vortexed and returned to the water bath for 30 minutes. The reaction is then terminated by the addition of HCl (0.8N, 0.025 ml).

Extraction and concentration of $^{14}C$-labeled 5-HETE is performed as follows. First, a solution (5.01 ml) containing 2 parts ethyl acetate, 3 parts $CH_2Cl_2$ and unlabeled arachidonic acid (0.01 ml) is added to each tube. The tubes are capped and briefly vortexed. The contents of each tube are poured into a polypropylene column fitted with a porous polyethylene disc and Whatman phase separation filter paper. The organic phase is collected by gravity filtration into a conical centrifuge tube, while the aqueous phase is retained in the column by the phase separation paper. Each culture tube is rinsed once with the $EtOAc:CH_2Cl_2$ solution (no arachidonic acid) (0.1 ml) and the wash added to the column. The organic phase is concentrated (to 0.5 ml) using a Savant Speed Vac concentrator (Savant Instruments, Inc., Hicksville, NY).

After concentration of the organic phase, the tubes are vortexed and stored covered on ice. An aliquot (0.01 ml) is then removed for liquid scintillation counting in a Beckman LS7500 Liquid Scintillation Counter (Beckman Instruments Corp., Fullerton, CA). Based on the count, the number of $\mu l$ containing $1 \times 10^5$ cpm is calculated. This volume is applied to a silica gel covered glass plate in a 10 mm streak. The remaining fluid in the tube is measured via syringe and noted.

The TLC plate is placed in a chromatography chamber containing the following solvent system:

$CHCl_3:MeOH:HOAc:H_2O(v/v;90:9:1:0.65)$.

The plate is then air dried and counted on a Berthold Linear TLC Analyzer (Berthold Instruments, Inc., Pittsburgh, PA) for 30 minutes per lane. The integrated area of the 5-HETE band for each compound is converted to percent of control and analyzed. The concentration ($\mu M$) which produces a 50% inhibition of 5-HETE synthesis ($IC_{50}$), is determined.

| Concentration of Compound 1 | % Inhibition of 5-HETE Biosynthesis |
| --- | --- |
| $5 \times 10^{-7}$ M | 18 |
| $10^{-6}$ M | 29 |
| $5 \times 10^{-6}$ M | 68 |
| $10^{-5}$ M | 67 |
| $5 \times 10^{-5}$ M | 66 |

$IC_{50} = 3 \times 10^{-6}$ M

EXAMPLE 9

Effect of Test Compound on $H_2O_2$ Production by Neutrophils (PMNs)

The respiratory burst of phagocytic cells is induced during phagocytosis or upon stimulation with appropriate surface (membrane) active agents, including phorbol esters such as phorbal myristate acetate, chemotactic peptides or calcium ionophore. During this process molecular oxygen is converted to superoxide anion, which in turn yields hydrogen peroxide, hydroxyl radical and products of myeloperoxidase action. These activated oxygen species contribute to the cells microbiocidal activity. However they have also been reported to contribute to the inflammatory process and tissue destruction in rheumatic diseases [J. Fantone and P. Ward, Amer. J. Pathol., 107, 397–418 (1982)]. This assay measures the ability of a test compound to inhibit the respiratory burst process by its effect on hydrogen peroxide production.

Human neutrophils are prepared from venous blood according to standard procedures [Henson et al., Immunol; 121, 851 (1978)], and are adjusted to a concentration of $5 \times 10^6$ cells/ml in $H_2O_2$ detection medium [a phenol red containing medium (RPMI 1630) supplemented with phenol red to a final concentration of 25 $\mu g/ml$ and sufficient horseradish peroxidase (100 $\mu g/ml$) to permit essentially instantaneous trapping of $H_2O_2$ by the phenol red].

Three sets of tubes are prepared: (1) unstimulated control cells (with and without drug), (2) PMA-stimulated cells (with and without drug) and (3) Opsonized zymosan stimulated cells (with and without drug). Either 10 $\mu L$ stock solution of test compound or 10 $\mu L$ medium is added to the appropriate tubes, followed by 1 ml cells in each tube. The tubes are incubated at 37° C. for 15 minutes. To the PMA stimulated group 10 $\mu L$/tube $10^{-5}$M PMA is added. To the opsonized zymosan stimulated group 20 $\mu L$/tube 10 mg/ml opsonized zymosan is added. The tubes are mixed gently to disperse cells and stimulus (if any) and 100 $\mu L$ is pipetted into each of four microtiter plates. The plates are covered and incubated 1 hour at 37° C. in $CO_2$.

After the incubation period 10 $\mu L$ 1N NaOH is added to each test well to develop the color. A blanking well is made up of 110 $\mu l$ distilled water. The plates are mixed on a microtiter mixer for 5 seconds and read on a Dynatech microplate reader $\lambda_T/\lambda_R = 550/405$ nm.

Mean OD values are calculated for each set of quadruplicate wells. Any artifactural change in absorbance due to a direct drug effect on the detection system is subtracted out from the $\Delta OD$ of the stimulated cells+-drug tubes. The % inhibition of $H_2O_2$ release by PMA or opsonized zymosan is calculated relative to the "O drug" control for each stimulus as follows:

$$\% \text{ Inhibition} = 100 - \left[ \frac{\Delta OD \text{ (stimulated cells + drug)}}{\Delta OD \text{ (stimulated cells - drug)}} \times 100 \right]$$

| Compound | Opsonized Zymosan Stimulated Oxidative Burst | PMA Stimulated Oxidative Burst |
| --- | --- | --- |
| 1 | $IC_{50}$ 14 $\mu M$ | $IC_{50}$ 25 $\mu M$ |

EXAMPLE 10

Reverse Passive Arthus Reaction

The reverse passive arthus reaction is initiated by the interaction of antigen and antibody resulting in the formation of a precipitating immune complex, followed by fixation of complement, accumulation of leukocytes, edema and hemorrhage. The immunopathology of rheumatoid arthritis involves many of the parameters found in this reaction.

Test groups (5 rats per group) are dosed orally with compounds one hour prior to the sub-plantar injection into the right hind paw of rabbit anti-ovalbumin antibody (50 $\mu g$/0.1 ml). Immediately afterwards, ovalbumin (Sigma, #5503) (5 mg/0.2 ml) is injected i.v. via the tail vein. The right hind paw volume is measured at hourly intervals, from one to four hours after the injection of the immune reactants.

The change in paw volume for each animal is calculated by subtracting the zero hour paw volume (before injection) from the paw volume at the time of measurement. The mean of these values is calculated for each group. Results are expressed as percent inhibition of paw swelling compared to untreated controls.

| Dose of Compound 1 | % Inhibition Hour: | | | |
| --- | --- | --- | --- | --- |
| | 1 | 2 | 3 | 4 |
| 1 mg/kg | 17 | 19 | 26 | 10 |
| 30 mg/kg | 29 | 50 | 55 | 44 |
| 100 mg/kg | 7 | 48 | 55 | 22 |

EXAMPLE 11

Mouse Mastocytoma Cell Leukotriene Release

The MMC-16 cell line represents a convenient in vitro model for studying the lipoxygenase pathway and offers an effective screening method by which inhibitory test compounds can be identified.

Cultured MMC-16 cells are suspended in $Ca^{++}$ free phosphate buffer at a concentration of $10^7$ cells/ml. The cell suspension is distributed into plastic culture tubes, 1 ml/tube. Duplicate tubes are used for each drug concentration tested, with drug solution (0.2 ml) added to each tube. An ionophore control consists of $Ca^{++}$ free buffer (0.2 ml) added to two tubes, and a blank (0.4 ml $Ca^{++}$ free buffer) added to two tubes. $CaCl_2$ solution (0.1 ml) is added to the drug and ionophore control tubes, which are vortexed and incubated at 37° C. for 40 minutes. The tubes are then centrifuged at $1,000 \times g$ for 10 minutes, and the supernatants collected and added to 4 volumes of absolute ethanol. $LTC_4$ content is then assayed for by either radioimmunoassay or high performance liquid chromatography.

The assay of $LTC_4$ content in the supernatants from the ionophore control group shows a relatively high, maximal, uninhibited amount of $LTC_4$. The supernatants from the unstimulated cells from the blank tubes do not contain any $LTC_4$. A dose-dependent decrease in $LTC_4$ levels found in the drug group supernatants shows the drug to have inhibitory activity.

| Concentration of Compound 1 | % Inhibition $LTC_4$ Release |
| --- | --- |
| $10^{-6}$ M | 0 |
| $3 \times 10^{-6}$ M | 18 |
| $10^{-5}$ M | 67 |
| $3 \times 10^{-5}$ M | 100 |

$IC_{50} = 7 \times 10^{-6}$ M

What is claimed is:

1. 3-[2-(3',5'-di-tert-butyl-4'-hydroxyphenyl)ethenyl]pyridine.

2. An antiinflammatory composition of matter comprising an effective amount of 3-[2-(3',5'-di-t-butyl-4'-hydroxyphenyl)ethenyl]pyridine in a pharmaceutically acceptable carrier.

* * * * *